United States Patent [19]

Naumann et al.

[11] Patent Number: 4,889,872

[45] Date of Patent: Dec. 26, 1989

[54] 2,3,5,6-TETRAFLUOROBENZYL (+) 1R-TRANS-2,2-DIMETHYL-3-(2,2-DICHLOROVINYL)-CYCLOPROPANECARBOXYLATE

[75] Inventors: Klaus Naumann, Leverkusen; Wolfgang Behrenz, Overath, both of Fed. Rep. of Germany

[73] Assignee: Bayer Aktiengesellschaft, Leverkusen, Fed. Rep. of Germany

[21] Appl. No.: 154,813

[22] Filed: Feb. 11, 1988

[30] Foreign Application Priority Data

Feb. 19, 1987 [DE] Fed. Rep. of Germany ....... 3705224

[51] Int. Cl.$^4$ .................... C07C 69/743; A01N 53/00
[52] U.S. Cl. ..................................... 514/531; 560/124
[58] Field of Search ......................... 560/124; 514/531

[56] References Cited

U.S. PATENT DOCUMENTS

| 4,183,950 | 1/1980 | Naumann | 560/124 |
| 4,256,907 | 3/1981 | Naumann | 560/124 |
| 4,370,346 | 1/1983 | Punja | 560/124 |
| 4,385,070 | 5/1983 | Bentley | 560/124 |
| 4,405,640 | 9/1983 | Punja | 560/124 |
| 4,567,199 | 1/1986 | Crowley | 560/124 |

FOREIGN PATENT DOCUMENTS

| 0017810 | 10/1980 | European Pat. Off. . |
| 0200943 | 11/1986 | European Pat. Off. . |
| 221635 | 5/1987 | European Pat. Off. ............ 560/124 |
| 2658074 | 7/1978 | Fed. Rep. of Germany . |
| 2379506 | 9/1978 | France . |
| 1567820 | 5/1980 | United Kingdom . |
| 2034700 | 6/1980 | United Kingdom ................ 560/124 |

OTHER PUBLICATIONS

European Search Report.
Pfianzenschutz-Nachrichten Bayer 35, 1982, pp. 309–313.
Pesticide Science, 1974, vol. 5, p. 796.
J. Chem. Soc. C, 1968, 1575.
Synthesis, 1985, 805.

*Primary Examiner*—Michael L. Shippen
*Attorney, Agent, or Firm*—Sprung, Horn, Kramer & Woods

[57] ABSTRACT

The novel compound 2,3,5,6-Tetrafluorobenzyl (+)1R-trans-2,2-dimethyl-3-(2,2-dichlorovinyl)-cyclopropanecarboxylate of the formula

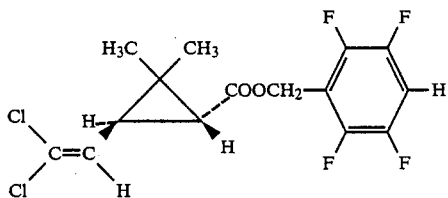

is highly active insecticidally.

11 Claims, No Drawings

2,3,5,6-TETRAFLUOROBENZYL (+) 1R-TRANS-2,2-DIMETHYL-3-(2,2-DICHLOROVINYL)-CYCLOPROPANECARBOXYLATE

The present invention relates to 2,3,5,6-tetrafluorobenzyl (+)1R-trans-2,2-dimethyl-3-(2,2-dichlorovinyl)-cyclopropanecarboxylate, a process for its preparation, and its use as an insecticide.

It has already been disclosed that esters of 2,2-dimethyl-3-(2,2-dichlorovinylcyclopropanecarboxylate) with polyfluorinated benzyl alcohols have insecticidal properties (in this respect, see German Patent Specification 2,658,074 and British Patent Specification 1,567,820). The pentafluorobenzyl ester exhibits an excellent action here since only a fifteenth of it killed flies in the same time as a mixture of equal parts of the 2,3,5,6-tetrafluorobenzyl and 3,5,6-trifluorobenzyl ester. The tetrafluorobenzyl ester alone likewise exhibits a good insecticidal action.

It is furthermore known that pentafluorobenzyl (−)1R-trans-2,2-dimethyl-3-(2,2-dichlorovinyl)-cyclopropanecarboxylate is highly suitable for combating household, hygiene and stored-product pests (Behren, Haumann, Pflanzenschutznachrichten Bayer 35, Leverkusen, 309–313 (1982). However, it is also known, for the same publication, that this active compound has a relatively high toxicity to mammals, (oral $LD_{50}$ in mg/kg for rats: 90–105). The cis/trans mixture of the corresponding 2,3,5,6-tetrafluorobenzyl ester has an even higher toxicity (oral $LD_{50}$ in mg/kg for male rats: 10–25). Nevertheless, the use of such toxic active compounds in household, hygiene and stored-product protection agents need not be prohibitive if they are employed in appropriately low dosages. However, it is the task of research to search for more and more nontoxic substances which have a greater and greater gap between an effective dose for the pest on the one hand and a toxic action for humans and animals on the other hand, i.e. which have a very good therapeutic index, since the safety in using such compounds is thereby increased.

The new 2,3,5,6-tetrafluorobenzyl (+)1R-trans-2,2-dimethyl-3-(2,2-dichlorovinyl)-cyclopropanecarboxylate of the formula (I)

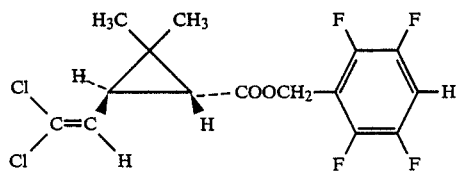

has now been found.

2,3,5,6-Tetrafluorobenzyl (+)1R-trans-2,2-dimethyl-3-(2,2-dichlorovinyl)-cyclopropanecarboxylate of the formula (I)

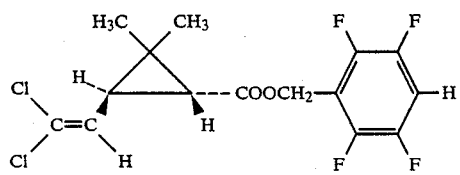

is obtained when (a) either (+)1R-trans-permethrin acid chloride of the formula

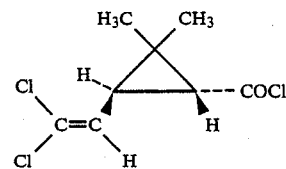

is reacted with 2,3,5,6-tetrafluorobenzyl alcohol of the formula

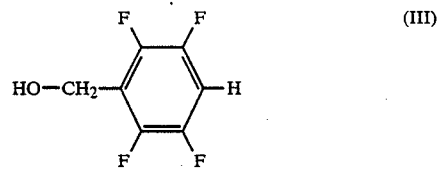

at temperatures between 20° and 100° C., or (b) the salt of (+)1R-trans-permethrin acid of the formula

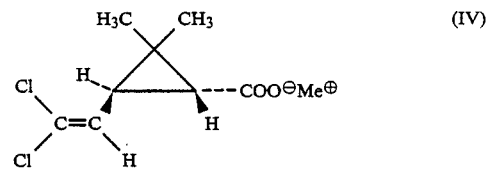

in which Me⊕ represents a monovalent cation, is reacted with a compound of the formula

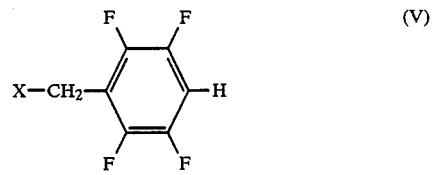

in which

X represents an anionically removable radical.

The new 2,3,5,6-tetrafluorobenzyl (+)1R-trans-2,2-dimethyl-3-(2,2-dichlorovinyl)-cyclopropanecarboxylate exhibits a surprisingly favorable therapeutic index since it has an extremely low toxicity to mammals along with a high activity (oral $LD_{50}$ in mg/kg in male rats: greater than 5000!).

Its toxicity to mammals is thus more than 250 times lower than that of tetrafluorobenzyl cis/trans-2,2-dimethyl-3-(2,2-dichlorovinyl)-cyclopropanecarboxylate and 50 times lower than that of pentafluorobenzyl (−)1R-trans-2,2-dimethyl-3-(2,2-dichlorovinyl)-cyclopropanecarboxylate. On its own, this would not be so surprising if the new compound claimed were also to lose activity against harmful organisms to the same extent. However, this is not the case. On the contrary, the more toxic tetrafluorobenzyl cis/trans-2,2-dimethyl-3-(2,2-dichlorivinyl)-cyclopropanecarboxylate has a lower biological action than the less toxic tetrafluorobenzyl (+)1R-trans-2,2-dimethyl-3-(2,2-dichlorovinyl)-cyclopropanecarboxylate according to the invention. Compared to pentafluorobenzyl (−)1R-trans-3-(2,2- dichlorovinyl)-cyclopropanecarboxylate, tetrafluorobenzyl (+)1R-trans-2,2-dimethyl-3-(2,2-dichlorovinyl)-cyclopropanecarboxylate of the formula (I) has a comparable insecticidal action at the same or an only slightly higher dosage.

The provision of the new 2,3,5,6-tetrafluorobenzyl (+)1R-trans-2,2-dimethyl-3-(2,2-dichlorovinyl)-cyclopropanecarboxylate thus represents a great enrichment of the state of the art.

Preparation of 2,3,5,6-tetrafluorobenzyl (+)1R-trans-2,2-dimethyl-3-(2,2-dichlorovinyl)-cyclopropanecarboxylate may be represented by the following equations:

ducing being allowed to escape, the reaction product subsequently being worked up, preferably by distillation. The starting components in process variant (a) are preferably employed in equimolar amounts.

In process variant (b), the salts (in particular the alkali metal salts) of (+)1R-trans-permethin acid are preferably reacted with 2,3,5,6-tetrafluorobenzyl chloride, bromide or tosylate, likewise preferably in equimolar amounts, in the sense of an esterification reaction, analogously to the procedure from Synthesis 1985, 805, in the presence or absence of an alkylation catalyst.

In the starting compounds of the formula (IV), Me⊕ preferably represents a monovalent metal cation and in

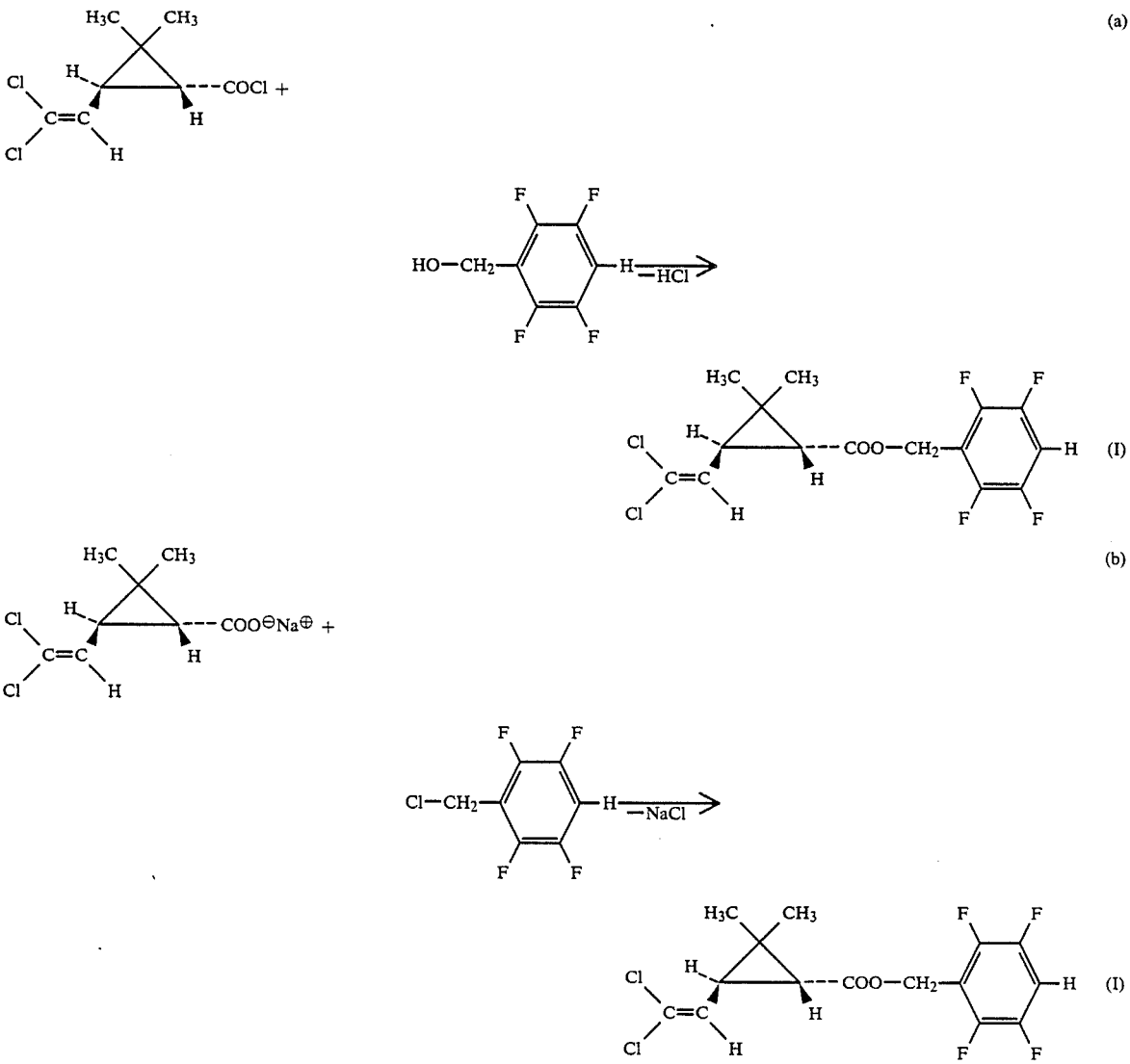

In process variant (a), (+)1R-trans-permethrin acid chloride, known from Pesticide Science 1974, 796, is reacted with 2,3,5,5-tetrafluorobenzyl alcohol known from J. Chem. Soc. C. 1968, 1575, at temperatures between 20° and 100° C. in the presence or absence of solvents and if appropriate in the presence of acid-binding agents.

In this process variant, the components are preferably reacted at temperatures between 30° and 80° C. in the absence of solvents and acid-binding agents, the volatile components (preferably hydrogen chloride gas) proparticular represents an alkali metal cation, where Na⊕ may be mentioned as an example.

In the starting compounds of the formula (V), X preferably represents halogen, in particular chlorine or bromine, or the tosylate radical (=radical of p-toluenesulphonic acid).

The reaction according to process variant (b) is preferably carried out in a solvent, in particular in a polar organic solvent which is inert for the reaction. The following may be mentioned as examples: acetonitrile, acetone and dimethylformamide.

Here also, the preferred work-up of the compound of the formula (I) produced is distillation.

Both variants (a) and (b) are preferably carried out at atmospheric pressure.

The active compound according to the invention is suitable for combating animal pests, in particular insects, which occur in the household or as hygiene or stored-product pests. It is active against normally sensitive and/or resistant species and against all or some stages of development. The abovementioned pests include:

From the order of the Thysanura, for example, *Lepisma saccharina*.

From the order of the Orthoptera, for example, *Blatta orientalis, Periplaneta americana, Leucophaea maderae, Blattelle geramnica* and *Acheta domesticus*.

From the order of the Dermaptera, for example, *Forficula auricularis*.

From the order of the Isoptera, for example, Reticulitermes spp.

From the order of the Anoplura, for example, *Pediculus humanus corporis*.

From the order of the Heteroptera, for example, *Cimex lectularius, Rhodnius prolixus* and *Triatoma infestans*.

From the order of the Lepidoptera, for example, *Ephestia keuhniella* and *Galleria mellonella*.

From the order of the Coleoptera, for example, *Anobium punctatum, Rhizopherta dominica, Hylotrupes bajulus, Oryzaephilus surinamensis,* Sitophilus spp. Dermestes spp., Trogoderma spp. Anthrenus spp., Lyctus spp. *Niptus hololecus, Gibbium psylloides* and Tribolium spp.

From the order of the Hymenoptera, for example, *Monomorium pharaonis, Lasius niger* and Vespa spp.

From the order of the Diptera, for example, *Aëdes aegypti,* Anopheles spp., Culex spp., Musca spp., Fannia spp., Calliphora sppl, Lucilia spp., Chrysomyia spp., Stomoxys spp. and Tabanus spp.

From the order of the Siphonaptera, for example, *Xenopsylla cheopis* and Ceratophyllus spp.

The active compound according to the invention can be applied alone or mixed with other insecticides, such as phosphoric acid esters, carbamates, pyrethroids or arylpyrazoles.

When mixed with other insecticides, the following mixable components may be mentioned as examples.

Phosphoric acid esters: dichlorvos (DDVP), fenitrothion, malathion, chlorpyrifos, diazinon and methyl pyrmiphos.

Carbamates: propoxur, carbofuran, carbaryl and bendiocarb.

Pyrethroids: cyfluthrin, tetramethrin, allethrin, vaporthrin, terallethrin, bioresmethrin, esbiol, cypermethrin, alphamethrin, decis and permethrin.

In the combination of the active compound according to the invention with one or more insecticidal active compounds from the series comprising the phosphoric acid esters, carbamates and further pyrethroids, a synergistic increase in action may be achieved in certain cases.

As can be seen from Example A and Table 1, it was possible to achieve a synergistic increase in action, for example, by combining the active compound according to the invention with dichlorvos (DDVP).

In addition, it was possible to achieve a synergistic effect by combining the active compound according to the invention with propoxur and cyfluthrin.

For the preparation of ready-to-use formulations, the active compound, alone or combined with other active compounds, is converted into conventional formulations, such as solutions, emulsions macro- and microemulsions, wettable powders, suspensions, powders, dusting agents, foams, pastes, aerosols, oil-based sprays, suspension concentrates, natural and synthetic substances impregnated with active compound, in particular so-called slow release formulations, which release the active compound slowly in a metered amount, very fine capsules of polymeric substances, burning equipment, fumigating cartridges, fumigating cans, antimosquito coils, ULV formulations, cold mist and warm mist formulations, moth papers and evaporator tablets for use in electrically or chemothermally heated devices.

The formulations are prepared in a known fashion, for example by mixing the active compound with extenders, i.e. volatile solvents, liquefied gases under pressure and/or solid excipients, if appropriate using surface-active agents, i.e. emulsifiers and/or dispersants and/or foam-forming agents. When water is used as the extender, organic solvents, for example, can also be used as auxiliary solvents. Suitable liquid solvents are, in general: aromatics, such as xylene, toluene or alkylnaphthalenes, chlorinated aromatics and chlorinated aliphatic hydrocarbons, such as chlorobenzenes, chloroethylene or methylene chloride, aliphatic hydrocarbons, such as cyclohexane or paraffins, for example mineral oil fractions, alcohols, such as butanol or glycol and the ethers and esters thereof, ketones, such as acetone, methyl ethyl ketone, methyl isobutyl ketone and cyclohexanone, strongly polar solvents, such as dimethylformamide and dimethyl sulpoxide, and also water; liquefied, gaseous extenders or excipients are taken to mean those liquids which are gaseous at ambient temperature and under atmospheric pressure, for example aerosol propellant gases: such as halogenated hydrocarbons, such as butane, propane, nitrogen and carbon dioxide, the following may be mentioned as solid excipients: ground natural minerals, such as kaolins, clays, talc, chalk, quartz, attapulgite, montmorillonite or diatomaceous earth, and ground synthetic minerals, such as highly disperse silica, alumina and silicates; suitable solid excipients for granules are crushed and fractionated natural rocks, such as calcite, marble, pumice, sepiolite and dolomite, and also synthetic granules of inorganic and organic meals, and granules or organic material, such as sawdust, coconut shells, corn cobs and tobacco stalks; suitable emulsifiers and/or foam-forming agents are nonionogenic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and albumin hydrolysates; and suitable dispersants are, for example, lignin, sulphite spent liquors and methylcellulose.

Adhesives, such as carboxymethylcellulose, natural and synthetic polymers in the form of powders, granules or latices, such as gum arabic, polyvinyl alcohol and polyvinyl acetate, can also be used in the formulations.

Commercially available ready formulations or the concentrates intended for further dilution generally contain 0.005 to 96% by weight of active compound, preferably between 0.02 and 90%.

The active compound content in the use forms prepared from commercially available formulations can vary within broad limits. The active compound concentration in the use forms can be from 0.001 to 100% by weight of active compound, preferably between 0.01 and 20% by weight.

Application takes place in a customary manner appropriate for the use forms.

Spray formulations and evaporator tablets are particularly preferred.

The following formulation examples may be mentioned as examples.

In these, the active compounds I to VI shown below are employed.

Active compounds

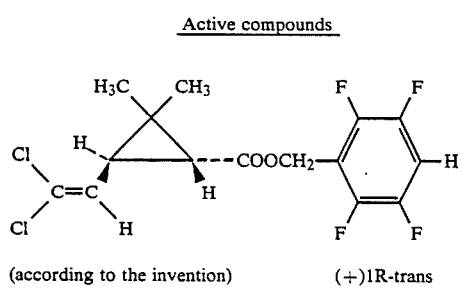

(according to the invention)  (+)1R-trans   I

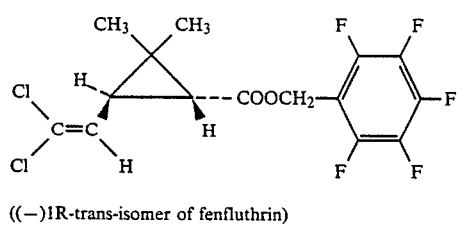

((−)1R-trans-isomer of fenfluthrin)   II

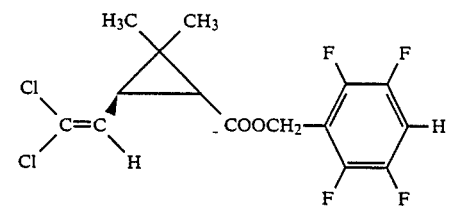

(±)cis/trans mixture   III

CH₃O O
    \\ ||
     P—O—CH=CCl₂
    /
CH₃O (diclorvos)   IV

H₃C    O
  \\   ||
   N—C—O—
  /              \\
 H                \\
                   \\
                    O——CH—CH₃
                         \\
                          CH₃

(propoxur)   V

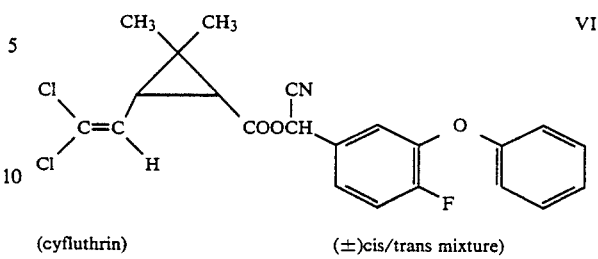

(cyfluthrin)   (±)cis/trans mixture   VI

| Formulation examples | Parts by weight in % |
|---|---|
| 1. Spray formulation | 0.04 |
| Active compound I | |
| Deodorized kerosene/mixture | 5.0 |
| of saturated, aliphatic hydrocarbons | |
| Perfume oil | 0.01 |
| Stabilizer | 0.1 |
| Propellant: propane/butane 15:85 | 94.85 |
| 2. Spray formulation | |
| Active compound II | 0.04 |
| Deodorized kerosene/mixture | 5.0 |
| of saturated, aliphatic hydrocarbons | |
| Perfume oil | 0.01 |
| Stabilizer | 0.1 |
| Propellant: propane/butane 15:85 | 94.85 |
| 3. Spray formulation | |
| Active compound III | 0.04 |
| Deodorized kerosene/mixture | 5.0 |
| of saturated, aliphatic hydrocarbons | |
| Perfume oil | 0.01 |
| Stabilizer | 0.1 |
| Propellant: propane/butane 15:85 | 94.85 |
| 4. Spray formulation | |
| Active compound IV | 1.0 |
| Deodorized kerosene/mixture | 5.0 |
| of saturated, aliphatic hydrocarbons | |
| Perfume oil | 0.01 |
| Stabilizer | 0.1 |
| Propellant: propane/butane 15:85 | 93.89 |
| 5. Spray formulation | |
| Active compound I | 0.04 |
| Active compound IV | 1.0 |
| Deodorized kerosene/mixture of | 5.0 |
| saturated, aliphatic hydrocarbons | |
| Perfume oil | 0.01 |
| Stabilizer | 0.1 |
| Propellant: propane/butane 15:85 | 93.85 |
| 6. Spray formulation | |
| Active compound II | 0.04 |
| Active compound IV | 1.0 |
| Deodorized kerosene/mixture of | 5.0 |
| saturated, aliphatic hydrocarbons | |
| Perfume oil | 0.01 |
| Stabilizer | 0.1 |
| Propellant: propane/butane 15:85 | 93.85 |
| 7. Spray formulation | |
| Active compound V | 1.0 |
| Active compound VI | 0.025 |
| Deodorized kerosene/mixture of | 38.36 |
| saturated, aliphatic hydrocarbons | |
| Perfume oil | 0.03 |
| Stabilizer | 0.1 |
| Methylene chloride | 15.0 |
| Propellant: propane/butane 15:85 | 45.485 |
| 8. Spray formulation | |
| Active compound V | 1.0 |
| Active compound VI | 0.025 |
| Active compound I | 0.04 |
| Deodorized kerosene/mixture of | 38.36 |
| saturated, aliphatic hydrocarbons | |
| Perfume oil | 0.03 |
| Stabilizer | 0.1 |
| Methylene chloride | 15.0 |

| Formulation examples | Parts by weight in % |
|---|---|
| -continued | |
| Propellant: propane/butane 15:85 | 45.445 |
| 9. Spray formulation | |
| Active compound V | 1.0 |
| Active compound VI | 0.025 |
| Active compound II | 0.04 |
| Deodorized kerosene/mixture of Saturated, aliphatic hydrocarbons | 38.36 |
| Perfume oil | 0.03 |
| Stabilizer | 0.1 |
| Methylene chloride | 15.0 |
| Propellant: propane/butane 15:85 | 45.445 |
| 10. Evaporator tablet | |
| Active compound I | 10, 20 or 30 mg |
| Diisononyl phthalate | 150 mg |
| Perfume | 0.25 mg |
| Cellulose tablet (16 × 28 × 3 mm) | 800 mg |
| 11. Evaporator tablet | |
| Active compound II | 10 mg |
| Diisononyl phthalate | 150 mg |
| Perfume | 0.25 mg |
| Cellulose tablet (16 × 28 × 3 mm) | 800 mg |

EXAMPLE A

In each experiment, 3 wire cages each containing 20 resistant male Musca domestica are suspended in rooms of volume 30 m³. The room is then sprayed using spray cans containing active compounds I, II, III and IV or active compound mixtures I+IV; II+IV; V+VI; V+VI+I and V+VI+II according to formulation Examples 1–9.

The amount of spray applied per spray can is 12.4 g. After spraying, the rooms are sealed and the action of the spray mist on the flies observed continuously through windows. The number of minutes after which 50 and 95% of the animals had fallen onto their backs (knock-down effect) is recorded. After a tesst duration of 1 hour, the percentage of knocked-down animals is subsequently determined. The table below contains the values determined.

TABLE 1

| | Aerosol Test (Musca domestica, resistant) | | | |
|---|---|---|---|---|
| Active compounds | Amount of active compound applied, mg/30 m³ | 50% knock-down after minutes | 95% knock-down after minutes | % knock-down after 1 hour |
| I | 5 | 22' | 47' | 96 |
| I | 7.5 | 18' | 33' | 99 |
| II | 5 | 19' | 37' | 99 |
| III | 5 | 38' | 52' | 97 |
| IV | 124 | — | — | 22 |
| I + IV | 5 + 124 | 18' | 39' | 97 |
| I + IV | 7.5 + 124 | 14' | 24' | 99 |
| II + IV | 5 + 124 | 15' | 26' | 99 |
| V + VI | 124 + 3.1 | 18' | 27' | 100 |
| V + VI + I | 124 + 3.1 + 5 | 12' | 17' | 100 |
| V + VI + II | 124 + 3.1 + 5 | 10' | 15' | 100 |

EXAMPLE B

Small cellulose tablets containing active compound according to formulation examples Nos. 9 and 10 are placed on the hotplate of small electroevaporator ovens, producing temperatures of 130° and 160° C. The instruments ae connected to the mains via a socket and heated up in living rooms of equal size and equally equipped.

During the experiment, one window in the rooms remained open to the outside in the tilted position. Immediately after switching on the ovens, 2 wire baskets each containing 20 mosquitoes of the Aedes aegypti species, 3–4 days old, were hung in each room. The knock-down action on the mosquitoes was checked half or one hour later. After the oven had burnt for a longer period, fresh mosquitoes were again introduced in the same way into the rooms at certain times, and the activity was again tested after half or one hour. The temperature of the heating oven, the amounts of reactive compounds, the heating duration, the test time and the knockdown effect can be seen from the table below.

(%Knock-down: percentage of mosquitoes which have fallen onto their backs).

In the present test, active compounds I (according to the invention) and II ((−)1R-trans-isomer of fenfluthrin) were employed.

TABLE 2

| | | Vapor test (Aedes aegypti) | | | |
|---|---|---|---|---|---|
| Active compound I, amount in mg | heating oven temperature, °C. | Animals introduced after heating time of the oven in hours | Residence time of the animals in the room in hours | % knock-down | |
| | | | | Active compound I | Active compound II (10 mg) |
| 10 | 160 | 0 | 1 | 100 | 100 |
| | | 8 | 1 | 100 | 100 |
| | | 26 | 1 | 55 | 40 |
| 10 | 130 | 0 | 1 | 100 | 100 |
| | | 8 | 1 | 100 | 100 |
| | | 26 | 1 | 100 | 100 |
| | | 50 | 1 | 85 | 97 |
| 20 | 160 | 0 | 1 | 100 | 100 |
| | | 8 | 1 | 100 | 100 |
| | | 28 | 1 | 100 | 92 |
| 20 | 130 | 0 | 1 | 100 | 100 |
| | | 8 | 1 | 100 | 100 |

TABLE 2-continued

| Active compound I, amount in mg | heating oven temperature, °C. | Vapor test (Aedes aegypti) Animals introduced after heating time of the oven in hours | Residence time of the animals in the room in hours | % knock-down Active compound I | Active compound II (10 mg) |
|---|---|---|---|---|---|
|  |  | 26 | 1 | 100 | 100 |
|  |  | 50 | 1 | 100 | 95 |
| 30 | 160 | 0 | 0.5 | 100 | 45 |
|  |  | 8 | 0.5 | 100 | 100 |
|  |  | 28 | 0.5 | 100 | 92 |
|  |  | 32 | 0.5 | 100 | 47 |
| 30 | 130 | 0 | 0.5 | 97 | 65 |
|  |  | 8 | 0.5 | 100 | 100 |
|  |  | 26 | 0.5 | 100 | 97 |
|  |  | 50 | 0.5 | 92 | 75 |

PREPARATION EXAMPLES 2,3,5,6-Tetrafluoro-benzyl (+)1R-trans-2,2-dimethyl-3-(2,2-dichlorovinyl)-cyclopropanecarboxylate (other name: 2,3,5,6-tetrafluorophenyl) (+)(1R,3S)-3-(2,2-dichlorovinyl)-2,2-dimethylcyclopropanecarboxylate)

Variant (a)

227 g (1 mol) of (+)1R-trans-permethrin acid chloride (optical purity: 95%) is added dropwise to 180 g (1 mol) of 2,3,5,6-tetrafluorobenzyl alcohol at 40° C. Towards the end of the gas evolution, the mixture is heated to 100° C. in order to complete the reaction, and the reaction product is subsequently distilled. Boiling point: 135°/0.15.

352.4 g (95% of theory) of the title compound of melting point 32° C. [α]= +15.3° (C=0.5 CHCl₃)

IR data: 3080, 2695, 2935, 2895, 1735, 1620, 1510, 1465, 1430, 1395, 1385, 1345, 1290, 1270, 1230, 1180, 1120, 1025, 1050, 995, 850–950, 785.

Variant (b)

27 g (0.11 mol) of potassium (+)1R-trans-2,2-dimethyl-3-dichlorovinyl-cyclopropanecarboxylate and 20 g (0.1 mol) of 2,3,5,6-tetrafluorobenzyl chloride and also 0.005 mol of pentamethylmethylenetriamine are boiled for 5 hours in 70 ml of acetonitrile until the halogen compound is completely consumed.

The mixture is subsequently evaporated in a rotary evaporator, the residue is taken up in petroleum ether and extracted by shaking with water, and, after evaporating the organic phase, 367.3 g (90% of theory) of the title compound are obtained.

Melting point and physical data, see above.

It will be understood that the specification and examples are illustrative but not limitative of the present invention and that other embodiments within the spirit and scope of the invention will suggest themselves to those skilled in the art.

We claim:

1. 2,3,5,6-Tetrafluorobenzyl (+)1R-trans-2,2-dimethyl-3-(2,2-dichlorovinyl)-cyclopropanecarboxylate of the formula

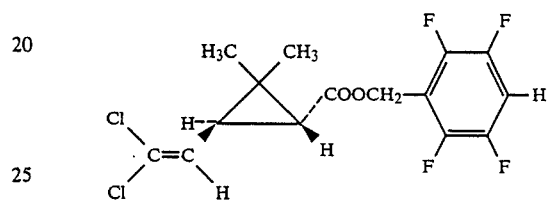

free of optical isomers.

2. An insecticidal composition comprising an insecticidally effective amount of 2,3,5,6-tetrafluorobenzyl (+)1R-trans-2,2-dimethyl-3-(2,2-dichlorovinyl)-cyclopropanecarboxylate according to claim 1 and a diluent.

3. An insecticidal composition comprising an insecticidally effective amount of 2,3,5,6-tetrafluorobenzyl (+)1R-trans-2,2-dimethyl-3-(2,2-dichlorovinyl)-cyclopropanecarboxylate according to claim 1 and at least one further insecticidally active compound selected from the group consisting of phosphoric acid esters, carbamates and further pyrethroids.

4. An insecticidal composition comprising an insecticidally effective amount of 2,3,5,6-tetrafluorobenzyl (+)1R-trans-2,2-dimethyl-3-(2,2-dichlorovinyl)-cyclopropanecarboxylate according to claim 1 and dichlorovos.

5. An insecticidal composition comprising an insecticidally effective amount of 2,3,5,6-tetraflurobenzyl (+)1R-trans-2,2-dimethyl-3-(2,2-dichlorovinyl)-cyclopropanecarboxylate according to claim 1 and propoxur.

6. An insecticidal composition comprising an insecticidally effective amount of 2,3,5,6-tetrafluorobenzyl (+)1R-trans-2,2-dimethyl-3-(2,2-dichlorovinyl)-cyclopropanecarboxylate according to claim 1 and cyfluthrin.

7. A method of combating insects which comprises applying to such insects or to an insect habitat an insecticically effective amount of the compound according to claim 1.

8. The method according to claim 7 wherein there is also applied a compound selected from the group consisting of phosphoric acid esters, carbamates and further pyrethroids.

9. The method according to claim 7, wherein there is also applied dichlorovos.

10. The method according to claim 7, wherein there is also applied propoxur.

11. The method according to claim 7, wherein there is also applied cyfluthrin.

* * * * *